(12) United States Patent  
Berg

(10) Patent No.: US 7,587,259 B2
(45) Date of Patent: Sep. 8, 2009

(54) ITEMS DISPENSER

(75) Inventor: Michel J. Berg, Rochester, NY (US)

(73) Assignee: University of Rochester, Rochester, NY (US)

(*) Notice: Subject to any disclaimer, the term of this patent is extended or adjusted under 35 U.S.C. 154(b) by 474 days.

(21) Appl. No.: 11/415,192

(22) Filed: May 2, 2006

(65) Prior Publication Data

US 2006/0259188 A1 Nov. 16, 2006

Related U.S. Application Data

(60) Provisional application No. 60/676,951, filed on May 3, 2005.

(51) Int. Cl.
*G06F 17/00* (2006.01)

(52) U.S. Cl. ............... 700/236; 700/240; 700/244; 221/7; 221/124; 221/194

(58) Field of Classification Search ............... 221/7, 221/124, 194; 700/240, 244, 236
See application file for complete search history.

(56) References Cited

U.S. PATENT DOCUMENTS

| | | | |
|---|---|---|---|
| 4,869,392 A | 9/1989 | Moulding, Jr. et al. | |
| 5,047,948 A | 9/1991 | Turner | |
| 5,084,828 A | 1/1992 | Kaufman et al. | |
| 5,267,174 A | 11/1993 | Kaufman et al. | |
| 5,405,048 A * | 4/1995 | Rogers et al. | 221/211 |
| 5,468,110 A | 11/1995 | McDonald et al. | |
| 5,480,062 A | 1/1996 | Rogers et al. | |
| 5,593,267 A | 1/1997 | McDonald et al. | |
| 5,661,978 A | 9/1997 | Holmes et al. | |
| 5,865,342 A * | 2/1999 | Ito et al. | 221/265 |
| 5,883,806 A | 3/1999 | Meador et al. | |
| 5,927,540 A | 7/1999 | Godlewski | |
| 5,940,306 A | 8/1999 | Gardner et al. | |
| 6,115,649 A | 9/2000 | Sakata | |
| 6,151,536 A | 11/2000 | Arnold et al. | |
| 6,163,737 A | 12/2000 | Fedor et al. | |
| 6,272,394 B1 | 8/2001 | Lipps | |
| 6,385,505 B1 | 5/2002 | Lipps | |
| 6,594,549 B2 | 7/2003 | Siegel | |
| 6,640,159 B2 | 10/2003 | Holmes et al. | |
| 6,732,884 B2 * | 5/2004 | Topliffe et al. | 221/3 |
| 6,758,370 B2 | 7/2004 | Cooke et al. | |
| 6,760,643 B2 | 7/2004 | Lipps | |
| 6,928,790 B2 * | 8/2005 | Takahashi et al. | 221/251 |
| 2004/0129716 A1 | 7/2004 | Naufel et al. | |

* cited by examiner

*Primary Examiner*—Gene Crawford
*Assistant Examiner*—Timothy R Waggoner
(74) *Attorney, Agent, or Firm*—Blank Rome LLP

(57) ABSTRACT

An automated small items dispensing apparatus is disclosed. In a preferred embodiment, the invention includes a networked, programmable, automatic medication items dispensing apparatus for use by individual patients who are enrolled in a medication protocol or medication therapy regimen. The device is located separate from the patient's health care provider's facility, such as in the patient's home.

6 Claims, 7 Drawing Sheets

FIG. 10

Patient Name / DOB / ID # / Pharmacy / Provider

| Med and size in mg | B or G | Use C or pm or titr | T1 8a | T2 N | T3 4p | T4 8p | Late or Miss med prot | Supply disp # / date of last refill | Refills remaining | # pills remains / bin # | Doses missed / pm usage past 30d | Last changes by whom | Cost total / patient | Notes |
|---|---|---|---|---|---|---|---|---|---|---|---|---|---|---|
| Med 1 / 10 mg | B | C | 2 | 1 | 2 | 3 | P1 | 1 month / 4/4/05 | 3 | 137 / bin 8 | 3 | In-creased Berg 3/23/05 | $1237 / $35 | Take with food |
| Med 2 / 350 mg | G | pm | | 2 at least 4 hours apart; maximum 8 per day | | | | #90 3/24/05 | 0 | 78 / bin 3 | 28 | Started 2/20/05 Oswald | $58 / $15 | Head or leg pain |
| Med 3 / 100 mg | B | titr | 2 | 1 (2) | 1 (2) | 2 | P2 | #240 3/24/05 | 5 | 188 / bin 10 | 1 | Started 3/24/05 Oswald | $245 / $25 | |
| New Med | | | | | | | | | | | | | | |

ITEMS DISPENSER

This application claims priority of provisional application Ser. No. 60/676,951 Filed May 3, 2005, which is hereby incorporated by reference.

BACKGROUND OF THE INVENTION

1. Field of Invention

The present invention relates to devices for dispensing items. In particular, the present invention relates to a networked, programmable, automatic medication items dispensing apparatus for use by individual patients who are enrolled in a medication protocol or medication therapy regimen at locations generally separate from a health care provider's facility, such as their homes.

2. Description of the Related Art

Almost half of the 3 billion prescriptions that are written each year by health care providers are taken incorrectly by patients. That negatively affects the health of the 46% of the American population that use prescription medication. It is estimated that health care providers spend about half of the time during regular appointments with prescription dependent patients discussing the patient's use of his or her medication protocol or medication therapy regimen. Accordingly, various dispensing devices have been developed to help patients adhere to those protocols or regimens.

Devices for dispensing small and large items are well know in the art. They include the ubiquitous vending machines used for automatically dispensing foods, drinks, tickets, and other items. In the health care industry, automated and manual dispensing devices are used for, among other things, segregating, controlling, and dispensing a wide range of medicaments, such as pills, vials, and packets. They are also used for managing the distribution and restocking of expensive instruments and laboratory supplies.

U.S. Pat. Nos. 6,163,737 and 5,047,948, for example, each disclose a system and apparatus for dispensing pills and medical supply equipment. U.S. Pat. No. 4,869,392 discloses a medication dispenser with main, selection, and exit compartments located within a housing.

Other related dispensing art is disclosed in U.S. Pat. Nos. 6,760,643; 6,758,370; 6,640,159; 6,385,505; 6,272,394; 6,151,536; 6,115,649; 5,940,306; 5,927,540; and 5,883,806.

U.S. Pat. No. 5,405,048 discloses a vacuum operated system for individually dispensing medicines from a bulk storage container to a user, where the medicine is dispensed under computer control, and the quantity and type of medicine is selected in advance by the user. The disclosed invention includes dispensing equipment and a computer that provides a user interface. Storage containers are arranged in a rotatable carousel or a rectilinear array that may contain various pharmaceutical articles, or various types, dosages, ages, and lot numbers of medicines. The patent discloses that after a user enters certain data into the computer, a universal vacuum probe is inserted within the storage container that contains the desired items, is lowered to the desired storage container, and engages with a container probe that is exclusive to that storage container. After a vacuum source creates suction within the universal vacuum probe and the container probe, the universal vacuum probe and the container probe individually extract items from the storage container.

Related U.S. Pat. Nos. 5,468,110 and 5,593,267 disclose a system for identifying and dispensing pre-coded packets containing medications that are stored in a dispensing facility, such as a pharmacy at a hospital. The system, which uses an optical bar-code reader, retrieves the individual packets using a vacuum system.

Programmable medical items dispensing devices have been around for a number of years. Many of them are computer operated and networked, allowing a remote operator to program and manipulate the devices by entering commands from a remote machine. However, none of those prior devices is adapted to being used by a patient at home who is enrolled in a prescribed medication protocol or medication therapy regimen under the supervision of a physician whereby the device is remotely programmable to allow the physician to modify the delivery of items to the patient over the course of time, that also has a restocking feature to minimize waste and enable counting of the number of items remaining in the bulk storage receptacle, and that also has other features for encouraging and monitoring a patient's adherence to his or her medication protocol or medication therapy regimen. Accordingly, there exists a need for such a device.

In particular, there exists a need for a system that provides an effective solution for both patients and health care providers regarding the patient's adherence or compliance with complicated medication regimens. Such a system should enhance the interaction between the patient and health care provider by allowing the health care provider to monitor the medication intake or modify the medication schedule, as well as by automating the storage and dispensing functions.

SUMMARY AND OBJECTS OF THE INVENTION

Accordingly, it is a principal object of the present invention to provide a dispenser for use by a patient at a location generally separate from the patient's health care provider and that allows the patient and the patient's health care provider to monitor and assure patient adherence or compliance with a prescribed medication protocol or medication therapy regimen.

It is another object of the present invention to provide a dispensing apparatus having storage receptacles containing different items, a number of temporary storage receptacles for receiving the different items from the storage receptacles, and a receptacle tray for receiving and then dispensing the different items to a person according to a time-sensitive prescribed protocol.

It is still another object of the present invention to provide a medication dispensing apparatus that enhances patient adherence to a prescribed medication protocol or medication therapy regimen while minimizing direct oversight by health care providers.

It is another object of the present invention to provide a dispensing apparatus having a microprocessor and motor(s) for automated control of the system.

It is still another object of the present invention to provide a communications device associated with a dispensing apparatus for allowing an operator, such as a health care provider or third party, to remotely control the automated functions of the dispensing apparatus and to receive status information from the dispensing apparatus.

It is another object of the present invention to provide a vacuum system incorporated into a dispensing apparatus for selectively moving a known quantity of items from one or more storage receptacles to a number of temporary storage receptacles or directly to a dispensing receptacle.

It is still another object of the present invention to provide a dispensing apparatus having an electronic input interface associated with a keyboard or keypad (for receiving instructions from a user), an input interface associated with a number of different instruments (for receiving electronic signals from the instruments such as a sphygmomanometer, glucometer, or other healthcare monitoring device), and an input interface associated with a microphone (for receiving oral commands using voice recognition technology) and a speaker for providing auditory information.

It is another object of the present invention to provide a dispensing apparatus having an electronic output interface associated with a display (for displaying information) and outputting an audible signal (such as an alarm or voice information/instructions).

It is still another object of the present invention to provide a dispensing apparatus that is adapted to reducing or increasing, over a pre-determined time period, the number and frequency of items being dispensed from the apparatus as in a medication titration.

It is another object of the present invention to provide a sensor for detecting the presence and weight of a dispensing tray in a dispensing apparatus to determine the number of pills in the tray.

Briefly described, these and other objects and features of the present invention are accomplished, as embodied and fully described herein, by a dispenser system having three main parts: (1) the dispenser; (2) a health care provider's interface; and (3) a human-machine interface. The system is capable of bulk storing, segregating, and temporarily storing medicaments (primarily solid, semi-solid, and liquid medications) for in-home use by a patient enrolled in a prescribed medication protocol or medication therapy regimen. The medicaments are either dispensed from the temporary storage receptacles to the user for distribution, or they are returned to the bulk storage receptacles for future use based on a user's, a third parties', or a physician's input. The dispenser is designed for a home environment. It is capable of communicating over the Internet (or by other telecommunications method such as a phone modem) through a user-friendly interface for remote monitoring and control. In one embodiment, it can stock up to three month's worth of preferably 24 different medications, which can be loaded in a bulk fashion from their original bulk packaging. It stores the pills in separate trays (receptacles) and it allows for their individual unloading. The device will alert the user of the dispenser, by several different means, of important actions such as medication to be taken, messages sent by the health care provider, or modifications made to their prescriptions or medication protocol or medication therapy regimen.

In a first embodiment of the invention, a central cylindrical hollow core is disposed within an outer core and is adapted to being slid along its longitudinal axis relative to the outer core. The hollow core is adapted to receive, on a first end, one or more small items. It is adapted to transport those small items through the hollow core by way of gravity or other means. It is adapted to dispense the small items through a second end into a fixed receptacle that is accessible by the user.

In a first resting position of the hollow core, the first end of the hollow core forms part of a wall of a plurality of temporary storage receptacles disposed around the periphery of the hollow core. In that position, the temporary storage receptacles are adapted to receive the small items from an associated bulk storage receptacle using a vacuum or other system.

In a second position of the hollow core, the first end of the hollow core is moved upward along its longitudinal axis thereby revealing an opening in the wall of the central core and causing the small items in one or more of the temporary receptacles to be displaced into the hollow core and dispensed as described above.

In a third position of the hollow core, the first end of the hollow core is instead moved downward along its longitudinal axis thereby revealing an opening to one or more bulk storage receptacles associated with each of the temporary storage receptacles and causing the small items to be displaced back into their bulk storage receptacles.

Thus, depending on which direction the hollow core is moved, the small items in the temporary storage receptacles will either be dispensed to the user or returned to bulk storage.

In the second embodiment of the invention, a longitudinally extending flat tray having a plurality of concave temporary storage receptacles is used to hold the small items. The tray is adapted to being rotated about its central longitudinal axis to one of three positions.

In a first neutral or resting position, a plurality of bulk storage receptacles are disposed on one side of the tray and a single or plurality of dispensing receptacles are disposed on the opposite side of the tray.

In a second position of the tray, the tray is rotated about its longitudinal axis in the direction of the dispenser containers thereby moving the temporary storage receptacles proximate the dispensing receptacles and causing the small items in one or more of the temporary receptacles to be displaced into the dispensing receptacles.

In a third position of the tray, the tray is instead rotated about its longitudinal axis in the direction of the bulk storage receptacles thereby moving the temporary storage receptacles proximate to the bulk storage receptacles and causing the small items in one or more of the temporary receptacles to be displaced back into the bulk storage receptacles.

Thus, depending on which direction the tray is rotated, the small items in the temporary storage receptacles will either be dispensed to the user or returned to bulk storage. Alternatively, the tray may have temporary storage receptacles that are adaptable to being opened such that the small items drop through an opening in the floor of the receptacles into either the dispensing receptacles or the bulk storage receptacles.

In the third embodiment of the invention, a removable tray is used having a plurality of receptacles that are adaptable to being temporary storage receptacles and dispensing receptacles. Rotating the tray about its longitudinal central axis causes the small items in the receptacles to be restocked in the bulk storage receptacles. Removing the tray allows the user to collect the contents of the receptacles. The removable tray may also be implemented in each of the other two embodiments described above.

Each of the embodiments additionally may include one or more of the following features: a sensor for detecting the presence and/or weight of the removable tray; a diagnostic instrument in communication with the apparatus, such as a portable heart or blood pressure monitor; an electric motor; a vacuum system; a microprocessor; input/output devices; an alarm; a communications device; associated software.

The vacuum system of the present invention is best implemented in one of two ways, although other methods not specifically mentioned are also contemplated. In the first implementation, the vacuum system is connected to an items selector that can be inserted into the bulk items storage receptacles from above the bulk items storage receptacles such that the vacuum system creates a vacuum at the tip of the items selector that is used to pull a single small item from the bulk items storage receptacles and deposit the same in the temporary storage receptacles. In the second implementation, the vacuum system is connected to an items selector that can be inserted into the bulk items storage receptacles from below the bulk items storage receptacles such that the vacuum system creates a vacuum at the tip of the items selector that is used to push a single small item from the bulk items storage receptacles and deposit the same in the temporary storage receptacles.

With these and other objects, advantages, and features of the invention that may become hereinafter apparent, the nature of the invention may be more clearly understood by reference to the following detailed description of the invention, the appended claims and to the several drawings attached herein.

BRIEF DESCRIPTION OF THE DRAWINGS

FIG. 10 is a drawing of a typical interface screen display used by a health care practitioner to enter commands and information into the dispensing apparatus of the present invention.

DETAILED DESCRIPTION OF THE PREFERRED EMBODIMENT

Figure 1:
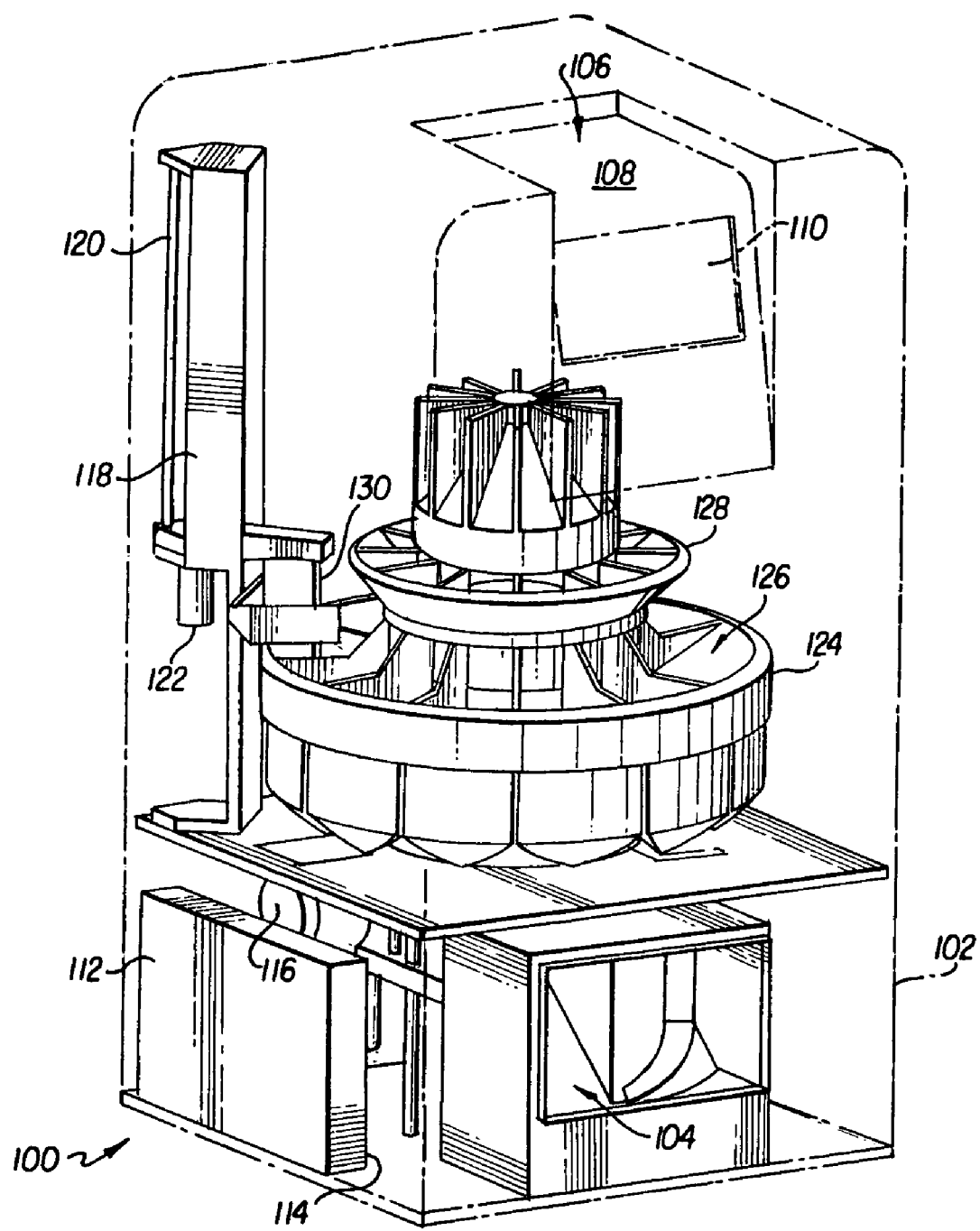
FIG. 1 is a perspective drawing of the dispensing apparatus according to one embodiment of the present invention.

Several preferred embodiments of the invention are described for illustrative purposes, it being understood that the invention may be embodied in other forms not specifically shown in the drawings.

Turning first to FIG. 1, shown therein is a perspective drawing of a dispensing apparatus (or "dispenser") 100 according to one embodiment of the present invention. The dispenser 100 has a rectangular housing 102. It is envisioned that the housing 102 can have any suitable size and shape that is different than that shown in FIG. 1 without deviating from the nature and scope of the invention. For example, the housing 102 could be cylindrically shaped and it could have a convex top, or it could be more squat and rectangular. The housing 102 should have a bottom surface that is capable of supporting the dispenser 100 on a flat surface, such as a desk or countertop, without the need for additional structure. It should form an interior space that is sufficiently large to completely enclose the structural components of the dispenser 100 (described below). Depending on the type of dispenser 100, the housing 102 may also provide for ventilation for heat-generating devices, insulate against heat transfer, be insulated to prevent electrical conduction, be insulated to minimize sound/noise conduction and be aesthetically pleasing.

The housing 102 includes a dispenser opening 104 located on at least one side or portion of the housing. Typically, the dispenser opening 104 is located near the bottom of the housing 102, especially where gravity is used to assist in dispensing items from the dispenser 100, but the dispenser opening 104 may also be located near the top of the dispenser 100 or at any other suitable location. The dispenser opening 104 provides a point of access between the interior of the dispenser 100 and the exterior of the dispenser 100. That is, the dispenser opening 104 allows a person to manually retrieve an item that was previously stored inside the dispenser 100. The dispenser opening 104 could include a device for closing or sealing the dispenser opening 104, such as a hinged or slidable door (not shown) that can be locked.

The housing 102 also includes a supply opening 106 located on at least one side or portion of the housing. Typically, the supply opening 106 is located near the top of the housing 102, or where it is convenient for a user or operator of the dispenser 100 to access the interior storage receptacles (described later). The supply opening 106 may include a hinged, lockable door 108 for closing or sealing the supply opening 106.

Positioned on or near the top of the dispenser 100, or at another appropriate location, preferably at a suitable angle for ease of use by a user or operator of the dispenser 100, is an interface communications device 110. The communications device 110 structure is used for accomplishing various interface functions. For example, the communications device 100 may include a transceiver or communications network interface card (not shown) for sending and receiving electronic instruction commands to and from a user or operator of the dispenser 100.

The communications device 110 may also include a keypad or keyboard (not shown) that allows the user or operator to input signals directly into the dispenser 100. The keypad buttons are simple momentary buttons.

The communications device 110 may also include a display, such as an liquid crystal display, for communicating information in the form of indicia (i.e., alpha-numeric, symbolic, etc.) relevant to the dispenser 100. A suitable liquid crystal display has an 8.times.24 character-based serial display.

The communications device 110 may also include an audible or visual alarm and a speaker. The alarm must produce a sound at a minimum of 65 dBA for a critical situation. Preferably, a gradually escalating alarm is used, which allows the user to set the volume depending on his or her hearing abilities. The frequency or tone should be between about 300-3,000 Hz. The visual alarm may simply be a backlit liquid crystal display.

Finally, the communications device 110 should include USB and PSt2 ports, or some other connectivity port developed or adopted in the future, and may include a variety of other ports such as infrared, serial, and other types that can be used for a barcode scanner, or other peripherals in future enhancements, or for electronic monitoring devices, such as pulse, respiration, blood glucose (glucometer), blood pressure (sphygmomanometer), and temperature instruments, and a scale.

Other features and aspects of the communications device 110 and the networking feature of the dispenser 100 are described in the companion patent application, U.S. patent application Ser. No. 11/415,191, filed concurrently herewith, the disclosure of which is incorporated herein by reference.

A printed circuit board 112 and a microprocessor 114 (not shown) are located inside the housing 102 of the dispenser 100. They are operatively connected to at least one direct current motor 116. The microprocessor 114 is used to control the various electronic devices of the dispenser 100 and their various functions. It is preferably an embedded microcomputer running a version of Linux that provides Ethernet and serial and 16 parallel inputs and outputs.

The operating software manages several different tasks. First it reads, processes, and outputs signals to and from the various communications devices such as the communications device 110. That may be accomplished by a non-blocking routine, which may be called from anywhere in the software, as long as it is called frequently enough to be transparent to the user. The actual menus being displayed may be stored as a doubly linked list that stores both the name to display and a pointer to a function, to run when that item is selected. The doubly linked list allows the menus to be created at any time based on the items currently stored in the dispenser 100. Being doubly linked, it can be traversed forward and backwards easily when the user presses the up and down buttons on the keypad.

Information about the items currently stored in the dispenser 100 may be stored in a flat text file. The information includes the location or position information of the items in the bulk items storage container 124 and the temporary storage container 128. The information also includes the name of the item, the size of the item, the quantity of the item to be dispensed, the frequency and time for dispensing the items, and a count of the total number of items. Where the item is a medication, the stored information also includes a flag if the medication is a pro re nata (PRN; or "take as needed") medication (e.g., a pain medication), the time between doses, the maximum number of that type of medication that can be taken per day, if any, the number of pills in the dispenser 100, the last time the medication was successfully taken, the half life of the medication, other relevant pharmacokinetic information, the dosing protocols, and a short note about how to take the medication. The dispenser will input all information about how to administer the medicaments, the standard timing for continuous medications, the rules for PRN medications (i.e., maximum dose and minimum time interval between doses), titration schedules for specific medications, late or missed medication protocols, information about previous doses that may affect subsequent doses, the times medications were actually taken (for a day or until such information is transferred for storage to a remote server), and display messages. The historical information about usage should be maintained in memory. Local storage of all the data, including a web server to interface with or alternatively store data on a remote third party server or on the health care practitioner workstation, may also be used. Storage on a remote server is preferred to ensure the integrity and accessibility of the data by health care practitioners.

Figure 2:
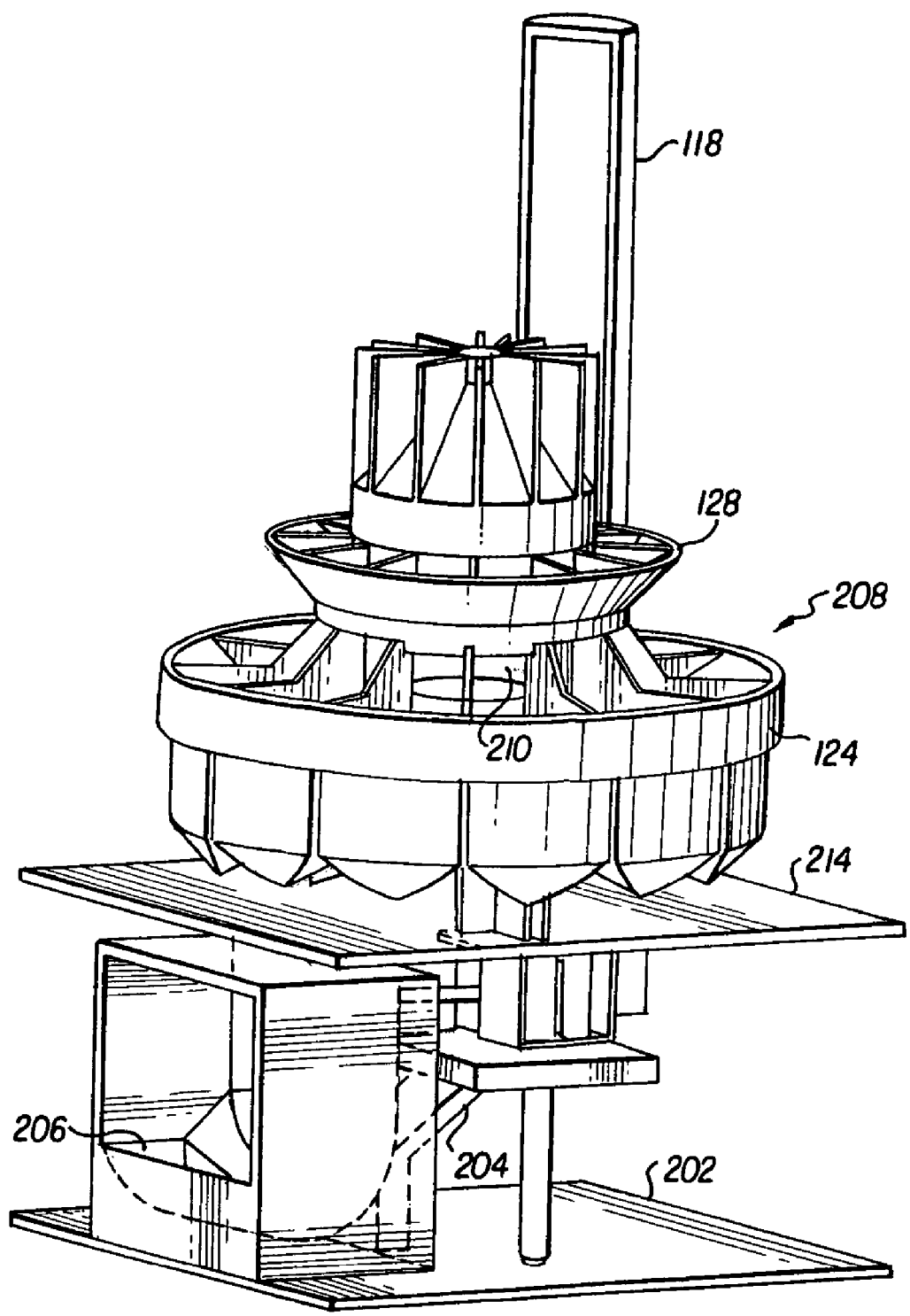
FIG. 2 is a perspective drawing of some of the structure making up the dispensing apparatus shown in FIG. 1.

Event logs contain entries for everything of note that occurred related to the dispenser 100. For example, each dispensed item that is removed from the dispenser 100 is logged, as well as when an item is dispensed and not removed. The log also records the time when items are retrieved to track if they are used earlier or later than scheduled or missed. Thus, if the predispensed items are called for (button push) they are immediately dropped into the dispenser tray 206 (as best seen in FIG. 2). Then if that dispenser tray 206 is removed (monitored) it is assumed to mean that the medicament was taken. The reason the dispenser tray 206 is monitored is to, among other things, know that it has been replaced so that subsequent dispensed items do not fall into the inside of the items dispenser 100 and cause a malfunction.

The motor 116 is used to dynamically move devices inside the dispenser 100 to pre-determined positions. The motor 116 may also be used to control ventilation, heating, and cooling of the system (i.e., by operating a ventilation fan (not shown), a heating coil fan (not shown), and a refrigeration system (not shown)). The motor 116 may also be used to generate a vacuum. The vacuum motor can be powered, for example, by a low side NMOS driver through a power MOSFET. Obviously, there may need to use multiple motors to accomplish the aforementioned requirements.

One of the devices inside the dispenser 100 that is dynamically moved by the motor 116 is the items selector 118. The items selector 118 performs various functions. Its primary function is to move selected items from one location to another within the dispenser 100. In the configurations shown in FIG. 1, the items selector 118 is interconnected to and slidably attached to a track 120, which could be a lead screw drive or other suitable device, that is mounted to the housing 102. Thus, the items selector 118 can be moved to any position along the track 120 in an up and down manner. Mechanical limit-switches are used to control the range of mechanical movement of the items selector 118 (another configuration for the items selector will be described in connection with the description of FIG. 4 below).

Figure 4:
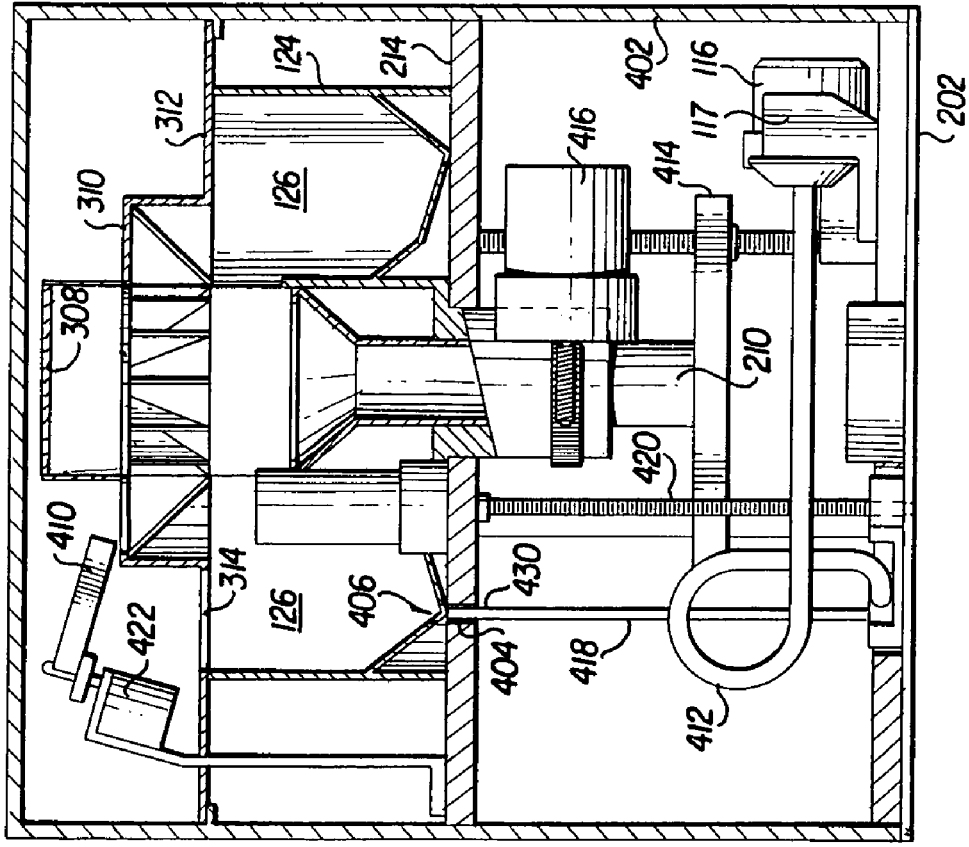
FIG. 4 is a cross-section perspective view drawing of the dispensing apparatus according to another embodiment of the present invention showing the dispensing apparatus in a pre-load configuration.

The items selector 118 includes a probe 130, which is a longitudinally-extending flexible, semi-rigid, or rigid hollow tube with a tip on one end. The other end is preferably connected to the aforementioned vacuum motor. U.S. Pat. No. 5,405,048 discloses a suitable device that could be modified for use in the dispenser 100 (suitable devices may be available from Cardinal Health-Pyxis Products, San Diego, Calif.). The vacuum system allows the tip of the items selector 118 (not shown) to physically connect with and pull a selected item. A vacuum port 122 may be interconnected to the vacuum system using a vacuum hose (as best seen in FIG. 4).

Instead of using a vacuum tip for the items selector 118, a mechanical pincher- or claw-like device that physically grips a selected item could be used. The appropriate structure of the items selector 118 will, in part, depend on the physical attributes of the selected item. Preferably, the selected item is a medicament, such as, but not limited to, a pill, tablet, or capsule, but it may also be a package (containing, for example, a pill, tablet, or capsule), vial, ampoule, bandage, or other item. The pills may range in size from a peppercorn to a large multi-vitamin. Thus, the items selector 118 may need to have a tip that is adapted to handle many different types and sizes of items.

Also located inside the housing 102 is a bulk items storage container 124. The bulk items storage container 124 is interconnected to the motor 116 using a worm gear set that allows it to be rotated 360 degrees in a carousel-like manner. Preferably, the motor 116 is provided with position sensors (not shown). The motor 116 rotates freely over the support 214 (FIG. 2) where it stands.

Figure 3:
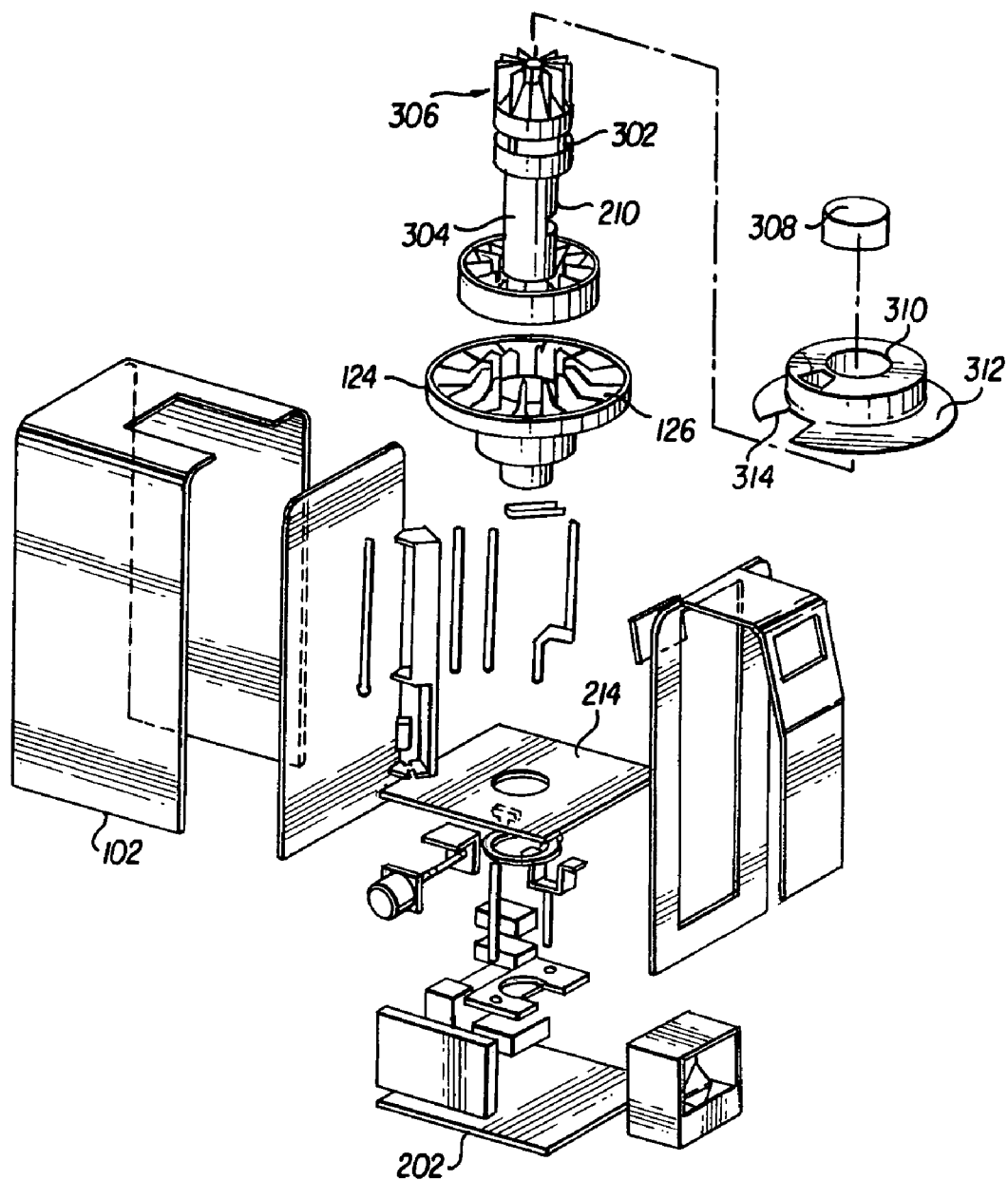
FIG. 3 is a partially exploded perspective view drawing of some of the structure making up the dispensing apparatus shown in FIG. 1.

The bulk items storage container 124 has several individual storage receptacles 126 that can be used to store different items (e.g., different types of medicines). The individual storage receptacles 126 may need to be watertight. The individual storage receptacles 126 may have removable inserts (not shown) in the same shape as the receptacles to facilitate cleaning. Preferably, the bottoms of the individual storage receptacles 126 are sloped so that the items inside the individual storage receptacles 126 are in close proximity to each other and as the supply of items diminishes the items selector can locate the last remaining items at the base of the slope (e.g. in the center). The entire bulk items storage container 124, or the individual storage receptacles 126 may be heated or refrigerated. The individual storage receptacles 126 are disposed at the periphery of the bulk items storage container 124. The top of each individual storage receptacle 126 can be left open as shown, but they may be closed using individual lids (as best seen in FIG. 3), if, for example, the content of the individual storage receptacle 126 is a liquid and also to prevent spillage if the dispenser 100 is tilted.

During initial and subsequent use of the dispenser 100, a user opens the lockable door 108, pours items through the supply opening 106 into the appropriate individual storage receptacles 126. A chute (not shown) is used between the lockable door 108 and the individual storage receptacles 126 to facilitate loading and avoid spillage. The entire bulk items storage container 124 then rotates to allow the user to load additional items.

Also located inside the housing 102 is a temporary storage container 128. The temporary storage container 128 is axially mounted above the bulk items storage container 124. Preferably, the temporary storage container 128 is divided into the same number of individual storage receptacles as the individual bulk storage receptacles 126 associated with the bulk items storage container 124. The temporary storage container 128 may be fixed, or be operated such that it rotates about the same axis as the bulk items storage container 124. Like the bulk items storage container 124, the top of each individual temporary storage receptacle can be left open as shown, but they may be closed using individual lids (as best seen in FIG. 3), if, for example, the content of the individual storage receptacle 126 is a liquid and also to prevent spillage if the dispenser 100 is tilted.

The housing 102 may also include a water storage tank, pump, and flow control devices (not shown) for use in reconstituting liquids.

Turning now to FIG. 2, shown therein is a perspective drawing of some of the structure making up the dispensing apparatus of FIG. 1. As shown in FIG. 2, the storage and dispensing features include a carousel 208, which includes the bulk items storage container 124 axially aligned with the temporary storage container 128 mounted on a longitudinally extending central hollow delivery chute 210 (a better view of the central hollow delivery chute 210 is contained in FIG. 3, described below). The entire apparatus is supported by support 214 and base 202. The delivery chute 210 is slidably engaged with respect to the bulk items storage container 124 and the temporary storage container 128. A dispensing ramp 204 is disposed between the bottom of the delivery chute 210 and an immovable or removable delivery tray 206.

FIG. 3 is a partially exploded perspective view of some of the structure making up the dispenser 100 shown in FIG. 1. The delivery chute 210 includes a longitudinally extending hollow member 304 connected to a head section 306. The head section 306 includes a plurality of openings 302 disposed around its circumference. Each opening is a through-hole extending to the interior hollow portion of the longitudinally extending hollow member 304. A sleeve or cover (not shown) can be used over the openings 302 to avoid mixing items between the individual storage receptacles 126, which could occur, for example, if the dispenser 100 is tilted and the openings 302 are aligned with the openings of individual storage receptacles 126.

At the top of the head section 306 is a cover or lid 308, which can be fixed or removably attached to the head section 306, to minimize spillage of items stored in temporary storage container 128. The lid 308 may cover the entire head section 306, or just part of it. As noted previously, individual lids can be used to cover each of the temporary storage receptacles of the temporary storage container 128. A shroud 310 is preferably installed over the temporary storage container 128 to prevent spills from the individual temporary storage receptacles when the dispenser 100 is tilted. The shroud 310 may include an opening that aligns with a single temporary storage receptacle during transfer of the items from the bulk items storage container 124. A shroud 312, which may be part of the shroud 310, may be installed over the bulk items storage container 124 to prevent spills from the bulk items storage receptacles 126 when the dispenser 100 is tilted. The shroud 312 may include an opening 314 that aligns with a single bulk items storage receptacle 126 during transfer of the items from the bulk items storage container 124 to the temporary storage container 128 (and is also used for loading the bulk items storage receptacles 126). A cover may be used to close the opening 314 and the opening on 310 when the dispenser 100 is not transferring items from the bulk items storage container 124 to the temporary storage container 128 or being loaded.

Some of the functional features of the present invention are now described.

The dispenser 100 is in data communication with a health care provider to allow patient communication with the health care provider and to allow the health care provider to perform various modifications to the dispenser 100 from a remote location. Data communications are preferably achieved by sending and receiving electronic data via a modem or by other telecommunications methods through a third party server (the data may also be uploaded directly into the system using a portable electronic storage medium device).

In the configuration of the invention shown in the embodiments of FIGS. 1-3 and FIGS. 4-7, the dispenser 100 preferably should be capable of storing about a 90-day supply of up to 12 unique items, such as 12 unique types of medications. More preferably, there will be at least 24 individual storage receptacles 126 on the bulk items storage container 124, and 24 temporary storage receptacles on the temporary storage container 128.

To bulk load the dispenser 100, the dispenser 100 identifies which item is presented (using, for example, an optical system or monitoring for a keypad entry from a user), aligns the appropriate individual storage receptacle 126 with the supply opening 106, allows the lockable door 108 to be opened, and receives the items (which are poured into the individual storage receptacles 126 in the manner previously described). Then, the entire bulk items storage container 124 rotates or resets to a neutral position to wait for the next item to be loaded. In the event an item, such as a particular medicament, is no longer used, the user can open the lockable door 108 and reach in and remove the individual temporary storage receptacle inserts to be emptied and cleaned. A lock and key sensor detects when the individual temporary storage receptacle inserts are returned to their proper position.

The dispenser 100 is not intended to operate like a typical food vending machine or so-called gumball machine that drops an item directly into the hand of the user. In many cases, that would not be practical where the patient may be suffering from biomechanical or neurological problems and where a large number of items are to be dispensed in any given time period. Thus, the dispenser 100 includes an immovable or removable dispensed items delivery tray allowing for a practical way of unloading the items from the temporary storage container 128. The delivery chute 210 may be segmented and drop the items from each individual temporary storage receptacle in the temporary storage container 128 into individual compartments in the delivery tray, which may also be segmented. Additionally, the delivery tray may be divided into different sections (e.g. to represent individual dose times) with its position controlled by a motor (not shown) to allow for preloading of several complete doses (e.g. each of the daily doses for an entire days supply of medications with each dose time in a separate compartment; the delivery tray may have closable lids over each section replicating a standard daily pill container design).

The dispenser 100 dispenses appropriate quantities (i.e., doses of medications) at pre-determined times and it will notify the user of the dispenser 100 of its activities by visual and/or auditory means. The process of dispensing involves a predispense procedure a period of time before the dose is due, where the appropriate medications are loaded from the bulk containers into the temporary storage container 128. This predispense procedure is relatively slow taking several minutes. At the appropriate time, the device alerts the patient that the medications are due to be administered. The patient then instructs the machine, preferable through a single button push, to dispense the medication dose. This step is rapid, taking only a few seconds, and involves sending the medications from the temporary storage container 128 into the delivery tray 206. The patient then removes the delivery tray 206, takes their medications and replaces the delivery tray 206.

The dispenser 100 is programmed and contains confidential health-related information. The information about the patient that is stored in the dispenser 100 remains confidential. Appropriate software with security and encryption, as needed, which limits access to the information via the communications device 110, is used.

All time-based events are recorded in an electronic storage device, preferably a database, inside the dispenser 100. The dispenser 100 provides programmability of at least, but not limited to, eight events per day, up to 20 dispensed items per event and as many of the same items as programmed (e.g., ten of the same pills per medication). The dispenser 100 is programmable in either absolute time or relative time.

The dispenser 100 is programmable to execute specific rules for treating late or missed medications, and to respond to input data, user messages/prompts and adherence/compliance actions. Although defaults may be offered, all of the rules require approval of the patient's physician or other qualified health care provider before implementation. For example, the following options may be selected for each rule related to a user who misses medications:

a) If dose is missed, do not make up;
 b) If dose is missed, administer 0 to ½ of the missed dose plus the next dose at the next time;
 c) If dose is missed, administer the missed dose plus the next dose at the next time.

Thus, rules may be set up depending on known pharmacokinetic properties of each specific medication such as the half-life of the items to be dispensed. For example, if the item has a half-life greater than 20 hours, select option c) above. If the item has a half-life greater than 8 hours but less than or equal to 20 hours, select option b) above. If the item has a half-life of less than or equal to 8 hours, select option a) above. The rules could easily be programmed with defaults based on intelligent pharmacokinetics and standard industry practices.

Other rules could be based solely on the time delay in retrieving items from the dispenser 100 after a scheduled dispensing time. For example, if the scheduled dose is 2-4 hours late, then the next dose will be prepared one hour late and an alarm will sound one hour late. If the scheduled dose is greater than or equal to 4 hours late, then the device will prepare a substitute dose according to:

a) If medication half-life is greater than 20 hours, guarantee a full daily dose;
 b) If medication half-life is greater than 8 hours but less than or equal to 20 hours, guarantee a dose, reduced by about 25%, aim for 75%, range 50-100%; and
 c) If mediation half-life is less than or equal to 8 hours, skip additional dosage and just administer a routine dosage.

The following are example rules that may be programmed into the dispenser 100. For Neurontin 400 milligrams (mg), having a half-life of 6 hours and a daily dose of 2/2/2/2 (number of pills per scheduled event), and where the patient misses the second dose (i.e., 2 pills or 800 mg) by 2-4 hours, then doses 3 and 4 are given one hour later than previously scheduled. If the patient misses the second dose by greater than 4 hours, then the patient would get a total of 6 pills in the day (i.e., the second dose is discarded).

For Phenobarbital 30 mg, having a half-life of 72 hours and a daily dose of three times (90 mg) per day, no matter when the patient takes the medication, the dispenser 100 ensures that the last dose of the day is dispensed so that the patient receives 90 mg for the day.

For Tegretol, having a half-life of 12 hours and a daily dose of 2 pills three times per day, and where the patient misses the second dose by 2-4 hours, then subsequent doses are given 1 hour later than previously scheduled. If the patient misses a dose by more than 4 hours, then the dispenser 100 ensures that the patient receives at least 50% of the missed dosage plus the remaining daily dose, with a target of receiving 75% of the daily dose.

The dispenser 100 is intrinsically electrically and mechanically safe to operate in a household environment. That is, it is electrically, thermally and sound insulated, and it does not have moving parts or other potential hazards exposed to the user.

The dispenser 100 is energized by means of a common household power source, but it is capable of operating with a power back-up system. That is especially important where the items being stored inside the dispenser 100 need to be maintained in a conditioned environment.

To prevent waste, the dispenser 100 automatically restocks items from the temporary storage container 128 to the bulk items storage container 124 when an item is not retrieved by the user within the appropriate time period. This is a cost effective means of avoiding producing wasted medications.

The dispenser 100 is programmable to automatically perform a system check on a routine basis. Status information is communicated to the user, the health care provider, and/or a third party, as needed.

The method of operating the dispenser 100 will now be described with reference to FIGS. 4-7. FIG. 4 is a cross-section perspective view of another embodiment of an items dispenser 400. Compared to the embodiment shown in FIGS. 1-3, the embodiment of the dispenser 400 shown in FIGS. 4-7 includes an items selector 418 that, like the items selector 118, is dynamically moved by the motor 116 in an up and down manner. The primary function of the items selector 418 is to move selected items from one location to another within the dispenser 400. In the configurations shown in FIG. 4, the items selector 418 is interconnected to and slidably attached to a gear 420, which could be a lead screw drive or other suitable device, that is mounted to the housing 402. Thus, the items selector 418 can be moved to any position along the gear 420. Mechanical limit-switches are used to control the range of mechanical movement of the items selector 418 within the space defined by the support 214 and the base 202.

The items selector 418 includes a probe 430 which is a longitudinally-extending flexible, semi-rigid, or rigid hollow tube with a tip on one end that is extendable through opening 404 on the support 214 and into an opening 406 disposed on the bottom of each of the bulk items storage containers 124. The opening 406 will have a door or be smaller than any of the items in the containers 124. The other end of the probe 430 is preferably connected to the aforementioned vacuum motor 117 via a vacuum tube 412. The vacuum system allows the tip of the items selector 418 to physically connect with and push upward a selected item stored in the bulk items storage containers 124.

Before an item is due to be dispensed according to a pre-programmed schedule, the microprocessor 114 activates the motor 416 and rotates the carousel 208 to a desired position. Then the motor 116 raises the tip of the items selector 418 into and through the appropriate individual storage receptacle 126 of the bulk items storage container 124. At the same time, the motor 116 activates the vacuum pump 117 to develop a suction through the vacuum tube 412 and a head pressure at the tip of the probe 430. The microprocessor 114 utilizes appropriate feedback transducers to detect when an item 508 (see FIG. 5) has been "captured" by the tip of the probe 430 of the items selector 418. At this point in the process, the delivery chute 210 is in a first position that is determined by the microprocessor 114, which sends instructions to the motor 416 to raise or lower the delivery chute 210. FIG. 4 also shows a hinged plate device 410 that, when the plates are abutting in a closed position forms a chute to enable the item to be transferred to the temporary storage container 128. When the hinge plates are in the abutting closed position, a small hole is present surrounding the items selector 418 such that no appreciable gap is present between the hinge plates of the hinge plate device 410 and the items dispenser 418. The hinged plate device 410 is controlled by the microprocessor 114 and operated by the motor 422.

Figure 5:
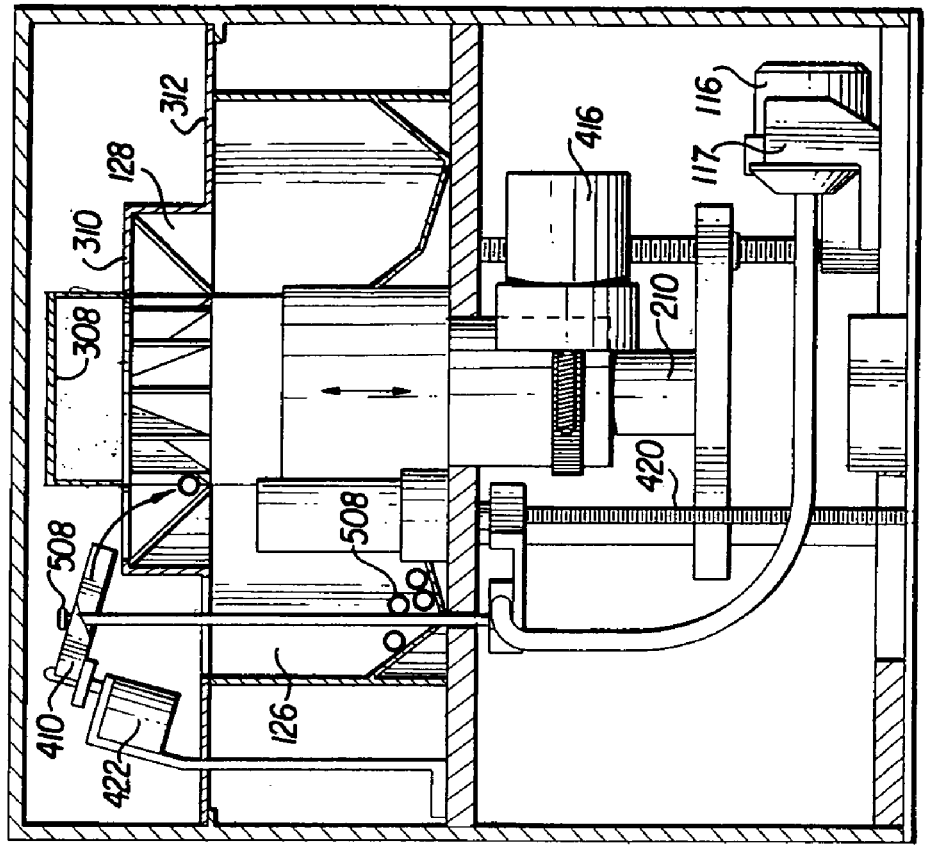
FIG. 5 is a cross-section perspective view drawing of the dispensing apparatus shown in FIG. 4 in which the items selector is in a fully-extended configuration.

As shown in FIG. 5, when an item 508 is captured by the items selector 418, it is moved vertically to a position proximate the hinged plate device 410 by way of the gear 420. The microprocessor 114 then turns the vacuum off either by tuning the vacuum pump 117 off, diverting the vacuum, or reversing the vacuum, which causes the selected item 508 to fall onto the hinged plate device 410 and into the temporary storage container 128. The hinged plate device 410 may also be used to remove the item 508 by first closing around the tip of the items selector 418 and then lowering the item selector 418. Thus, even if turning the vacuum off, diverting the vacuum, or reversing the vacuum does not cause the item 508 to fall into the temporary storage container 128, the hinged plate device 410 will force it off of the tip of the items selector 418.

Not shown in FIG. 5 is an optical recognition device or other sensor type that is used to sense the presence of the item 508 on the tip of the probe 430 as the item selector is moved into its upper-most position. Also not shown is a mass sensor associated with the items selector 418 or hinged plate device 410 that can detect an incremental change in weight of those devices, or another sensing device, as a means to sense the presence of the item 508.

The process of selecting an item 508 from the individual storage receptacles 126 is repeated until all the items for a specific, scheduled dispensing period are collected in the temporary storage containers 128. This pre-dispensed step is accomplished within a sufficient time period before the scheduled dispensing time (e.g., an hour before).

Figure 6:
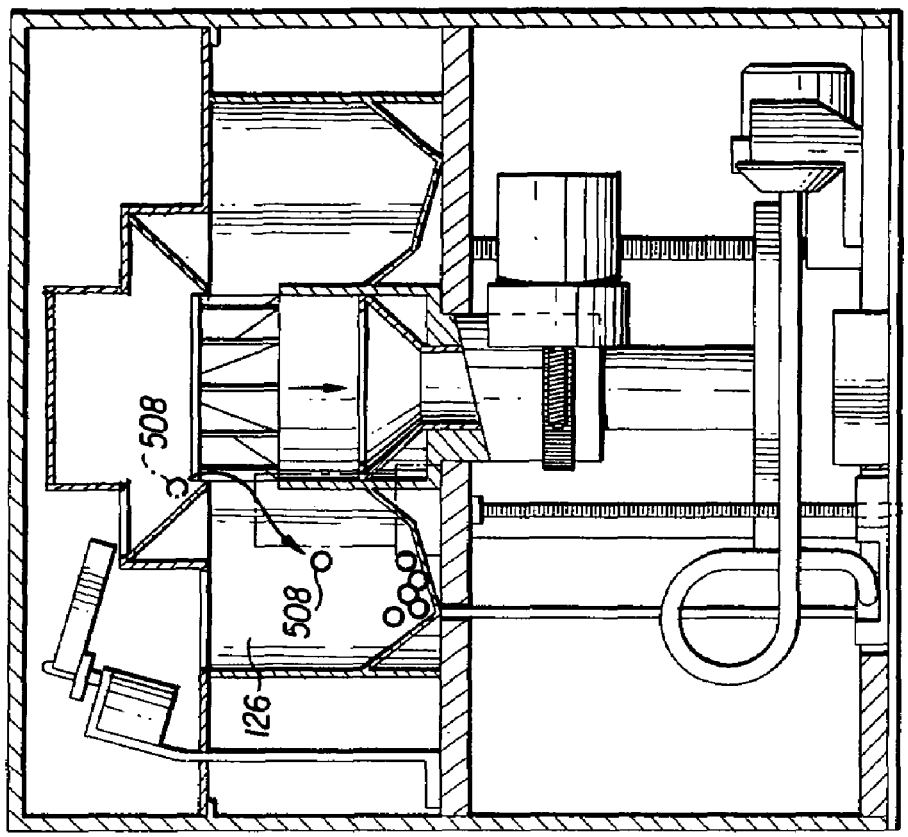
FIG. 6 is a cross-section perspective view drawing of the dispensing apparatus shown in FIG. 4 in which the dispensing apparatus is in a dispensing configuration.
Figure 7:
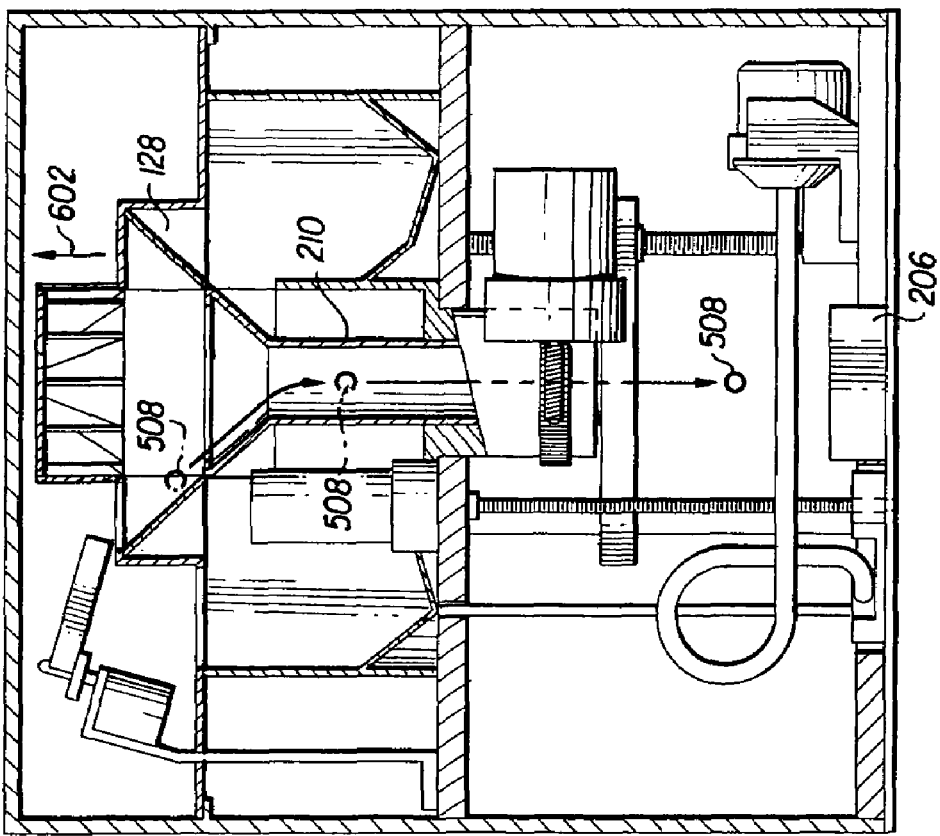
FIG. 7 is a cross-section perspective view drawing of the dispensing apparatus shown in FIG. 4 in which the dispensing apparatus is in a restocking configuration.

At the scheduled time, the microprocessor 114 then energizes the communications device 110, in particular the audible and/or visual alert component of the communications device 110, to inform the user that the items are ready to be retrieved. When the user presses an appropriate button on the keypad interface on the communications device 110, the microprocessor 114 activates the motor 416, which causes the delivery chute 210 to move vertically upward, as shown in FIG. 6 by the arrow 602, thereby allowing the item 508 in the temporary storage container 128 to move down the delivery chute 210 to the delivery tray 206 where it can be collected by hand. If the item 508 is not retrieved, after a predetermined amount of time (for example, one hour), then the microprocessor 114 activates the motor 416, which causes the delivery chute 210 to move downward, as shown in FIG. 7, thereby allowing the item 508 to slide back into the respective individual bulk items storage receptacles 126. Both of those events are recorded and the information may be sent to the health care provider or a third party for data storage and retrieval.

Figure 8:
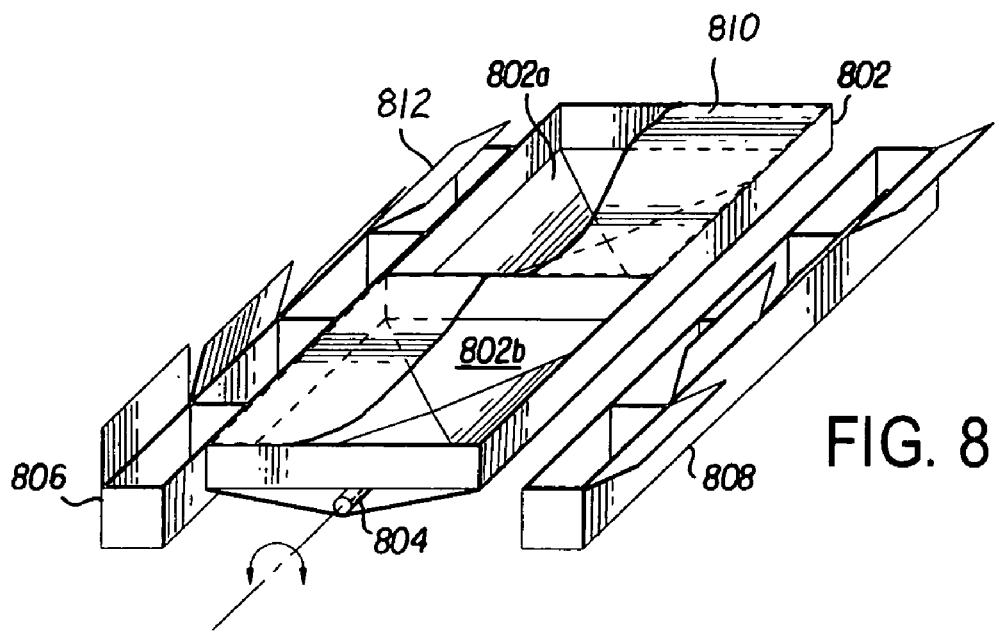
FIG. 8 is a partial perspective view drawing of another embodiment according to the present invention.

Turning now to FIG. 8, shown therein is a partial perspective view of another embodiment according to the present invention. In that embodiment, a temporary storage container 802 is rotatably mounted on a hinge or pivot 804 that is interconnected to the motor 116 (or motor 416). The temporary storage container 802 includes a plurality of individual temporary storage receptacles 802a, 802b. Although only two individual temporary storage receptacles are shown, one of ordinary skill in the art will appreciate that the temporary storage container 802 may include many more individual temporary storage receptacles. Preferably, each individual temporary storage receptacle 802a, 802b has a concave or sloped floor.

The temporary storage container 802 is disposed between a dispensing tray 806 and a bulk items storage container 808. Each bulk items storage receptacle includes a plurality of individual bulk items storage receptacles 808a, 808b, etc.

In operation, the microprocessor 114 activates the motor 116 and lowers the tip of the items selector 118 into the appropriate individual storage receptacle 808a, 808b, etc. within the bulk items storage container 808. At the same time, the motor 116 activated the vacuum pump 117 to obtain suction through the vacuum tube 412 (not shown). The microprocessor 114 utilizes appropriate feedback transducers to detect when an item has been captured by the tip of the items selector 118, 418.

If an item is captured by the items selector 118, 418, it is positioned proximate to one of the individual temporary storage receptacles 802a, 802b and dropped into the appropriate receptacle. That process is repeated until all of the items are properly placed into an appropriate temporary receptacle. At the appropriate time, the microprocessor 114 then energizes the communications device 110, in particular the audible and/or visual alert component of the communications device 110, to inform the user that the items are ready to be retrieved. The user then presses a button on the communications device 110 which activates the motor 116 and rotates the temporary storage container 802 and causes the items in the temporary storage container 802 to drop into the dispensing tray 806. The user can retrieve the dispensing tray 806, collect the items, and then return the dispensing tray 806 to the dispenser 100. If the items are not retrieved, after a pre-determined amount of time (for example, one hour), then the microprocessor 114 activates the motor 116 and rotates the temporary storage container 802 and causes the items in the temporary storage container 802 to drop into the bulk items storage container 808. Both of those events are recorded and the information is sent to the health care provider or a third party. Lids or covers 810, 812 may be used to prevent spills.

Figure 9:
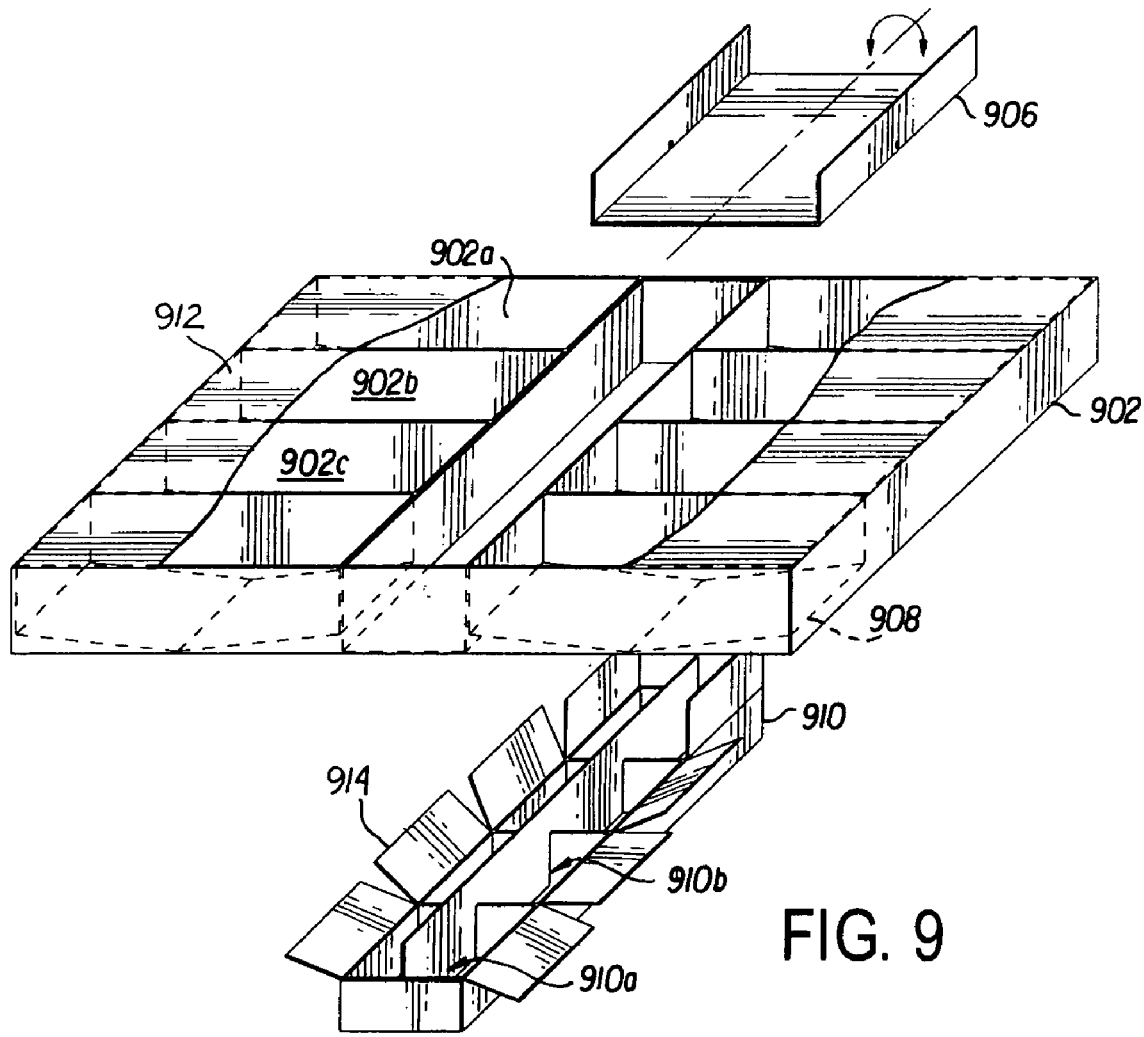
FIG. 9 is a partial perspective view drawing of still another embodiment according to the present invention.

FIG. 9 is a partial perspective view of still another embodiment according to the present invention. In that embodiment, a bulk items storage container 902, having two rows of individual bulk items storage receptacles 902a, 902b, etc. are located inside the dispenser 100. Each individual bulk items storage receptacle 902a, 902b, etc. preferably has a sloped or concave bottom as shown by the broken line 908.

A rotatable support tray 906 is disposed proximate the two rows of individual bulk items storage receptacles 902a, 902b, etc. The support tray 906 can be rotated in a clockwise or counter-clockwise manner.

A removable dispensing tray 910 is designed to be placed on the support tray 906. The dispensing tray has a plurality of individual dispensing tray receptacles 910a, 910b, etc. Lids or covers 912, 914 may be used to prevent spills.

A sensor transducer 914 (not shown) is used to detect the presence of the dispensing tray 910. One of ordinary skill in the art will appreciate that any suitable sensor could be used, including, but not limited to, an optical or mass sensor.

In operation, the user can retrieve the dispensing tray 910 after it is filled, collect the items, and then return the dispensing tray 910 to the dispenser 100. If the items are not retrieved, after a pre-determined amount of time (for example, one hour), then the microprocessor 114 activates the motor 116 and rotates the support tray 906 in a clockwise or counter-clockwise manner, allowing the items in the dispensing tray 910 to drop into the bulk items storage receptacle 902. Both of those events are recorded and the information is sent to the health care provider or a third party.

The communications device 110 interface will now be further described. Turning to FIG. 10, shown therein is a drawing of a typical graphical user interface (GUI) display used by a health care practitioner to enter commands and information into the dispenser 100 of the present invention. The GUI display shown is a patient selection screen 1002, which is displayed after a login screen. Preferably, the GUI screen 1002 is displayed on a client computer monitor located at a health care provider's facility that is in data communication with the dispenser 100 via a communications network, such as the Internet. A similar display can be provided on the communications device 110 on the dispenser 100.

The GUI screen 1002 shows three rows of information 1004, 1006, 1008, corresponding to three different items to be dispensed, in this case, medications (i.e., "Med 1," "Med 2," and "Med 3"). "B" refers to branded medications; "G" refers to generic medications; "C" refers to continuing use; "pm" refers to as-needed medications; "T1" refers to time 1, etc.; "prot" refers to protocol; "disp" refers to dispense; "P-a" refers to a defined protocol; and "titr" refers to titration in progress. One of ordinary skill in the art will understand that the specific types of information that may be displayed to the health care practitioner can vary from the information described above and shown in FIG. 10, or it can be displayed on different screens that may be drilled down from a first navigation screen or navigation tool displayed on the GUI screen 1002.

Several drill down menu selections are provided to the health care professional. For example:

C1: medication (select medication/dose from list of preferred medications (the device can include a comprehensive medication database listing medication names and pill sizes and if generic available, or access such a database from an Internet web site);

C2: select Brand or Generic (if generic available or alternative in medication list);

C3: usage (continuing or pm or titration; if pm then popup table for rules (# of pills, minimum time between doses, maximum number in a day; optimally, display this in time columns so all continuing meds listed first, pms at bottom; also have option here for titration;

C4: enter times (option for week or every day dosing, includes button for "other schedule"; 4.times.7 grid without dates but with day labels on top);

C8a: protocols for missed medications;

C9: supply (number of days or number of months or number of pills; if previously prescribed displays last supply and date of script or last refill; default blank field);

C10: refills (displays number of refills remaining if previously prescribed; default is zero);

C11: number of pills remaining in dispenser 100;

C12: missed doses in past 30 days for continuing medications;

C13: dose changes and by who;

C14: notes (entered by health care provider; to be displayed when items has been dispensed or pre-dispensed for).

Other drill-down menu options should include: pre-dispense items n hours prior to scheduled time; if item is a medication and is not taken within ×1 hours, shift dosing clock; if item is a medication and is not taken within ×2 hours, plan for adjusted dose. An option to call a pre-determined phone number of a relative or other third party if items are missed after three hours or after two consecutive doses are missed.

Another display screen allows the dispenser 100 to be programmed with personal information (security is provided to comply with HIPAA requirements):

Name;

DOB;

ID number;

pharmacy name and phone number (fax);

Dispenser 100 identification number;

Insurance info;

Price of items (insurance tier) to insurance and patient when prescribed.

Another drill down menu shows the current contents of each temporary storage receptacle and each bulk items storage receptacle. Yet another drill down menu shows a medication history. Still another drill down menu provides access history. Preferably, the display will include a final "Accept" button and confirmation message for the health care provider (e.g., changes sent to dispenser and pharmacy).

Text messages communicated to the user of the dispenser 100 on the communications device 100 (i.e., alpha-numeric-symbolic liquid crystal display screen) include changes to medication dose (e.g., automatic message to patient. "Dr. Berg has increased your Coumadin to 2 pills on Sunday and Thursday"; "Hi Ms. Clark, the INR was a little low at 1.7 so I increased the Coumadin"; "If you have any questions please call my office at 555-5555.—Dr. Berg"). Other messages remind the user to refill the dispenser 100 (e.g., "The refill of medication x, medication y, and medication z, should be ready at the Winton Road pharmacy (555-5555). You have only 6 days supply remaining of medication x, 5 days of medication y and 7 days of medication z.").

One of the important functions of the dispenser 100 is the ability of a health care provider to titrate the user's prescribed medication protocol or medication therapy regimen. For example, if a health care provider determines that a patient requires neurontin, the health care provider can enter a target dose and the changes to the prescribed medication protocol or medication therapy regimen to achieve that dose. The example below illustrates such a titration for Neurontin. TABLE-US-00001 EXAMPLE 1 Neurontin titration; days 10-12. Neurontin 8 AM Noon 5 PM 10 PM Target dose 800 800 800 1000 Days 1-3 200 Days 4-6 400 400 Days 7-9 400

400 400 400 Days 10-12 800 400 400 800 Days 13-15 800 800 800 800 Target dose 800 800 800 1000

Although certain presently preferred embodiments of the disclosed invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

I claim:

1. An automated items dispensing apparatus comprising:
    at least one storage receptacle containing an item;
    a longitudinally extending hollow first member having a plurality of through holes disposed on a proximate end of the first member, wherein the first member is displaceable between a first position and a second position;
    at least one temporary storage receptacle proximate the at least one storage receptacle, wherein the temporary storage receptacle has a first opening for receiving the item from the storage receptacle and a second opening for discharging the item to one of the plurality of through holes, and wherein the second opening and the one of the plurality of through holes are aligned upon the first member being advanced from the first position to the second position which allows the item to discharge from the second opening to the aligned one of the plurality of through holes;
    a vacuum device for transferring the item from the at least one storage receptacle to the at least one temporary storage receptacle; and
    a dispensing receptacle adjacent a distal opening of the first member for receiving the discharged item.

2. A method of dispensing an item according to a predetermined dispensing protocol, comprising the steps of:
    providing an automated dispensing apparatus comprising:
        at least one storage container containing the item;
        a longitudinally extending hollow first member having a plurality of through holes disposed on a proximate end of the first member, wherein the first member is displaceable between a first position and a second position;
        a temporary storage container proximate each of the plurality of through holes, wherein the temporary storage container has a first opening for receiving the item from the storage container and a second opening for discharging the item to one of the plurality of through holes, and wherein the second opening and the one of the plurality of through holes are aligned upon the first member being advanced from the first position to the second position; and
        a dispensing receptacle adjacent a distal opening of the first member for receiving the item;
    causing the item to be moved from the storage container to the temporary storage container;
    notifying a user of the item;
    upon receiving an instruction from the user, advancing the first member to the second position and dispensing the item to the user; and
    upon failing to receive an instruction from the user, advancing the first member to a third position and restocking the item in the storage container.

3. The method according to claim 2, wherein the step of advancing the first member to the second or third positions is accomplished by a motor interconnected to the first member.

4. The method according to claim 2, wherein the item is one of a medication package, individual tablet, and individual capsule.

5. The method according to claim 2, wherein the step of causing the item to be moved from the storage container to the temporary storage container is accomplished by a vacuum device having a tip for retrieving the item; and a hinged plate device for directing the item away from the probe and into the temporary storage container.

6. A method of dispensing an item according to a predetermined dispensing protocol, comprising the steps of:
    providing an automated dispensing apparatus comprising:
        at least one storage container containing the item;
        at least one temporary storage container;
        at least one dispensing receptacle spaced apart from the at least one storage container; and
        a longitudinally extending first member disposed between the at least one storage container and the at least one dispensing receptacle and having at least one individual temporary storage receptacle, wherein the first member is rotatable about its longitudinal axis between a first position and a second position, whereby in the first position the first member is adapted to receive the item into the at least one individual temporary storage receptacle, and in the second position the first member is adapted to discharge the item from the at least one temporary storage container into the at least one dispensing receptacle;
    causing the item to be moved from the storage container to the temporary storage container;
    notifying a user of the item;
    upon receiving an instruction from the user, rotating the first member to the second position and dispensing the item to the user; and
    upon failing to receive an instruction from the user, advancing the first member to a third position and restocking the item in the storage container.

* * * * *

UNITED STATES PATENT AND TRADEMARK OFFICE
CERTIFICATE OF CORRECTION

PATENT NO. : 7,587,259 B2
APPLICATION NO. : 11/415192
DATED : September 8, 2009
INVENTOR(S) : Michel J. Berg It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 527 days.

Signed and Sealed this

Twenty-first Day of September, 2010

David J. Kappos
*Director of the United States Patent and Trademark Office*